US012773263B2

(12) United States Patent
Ozeri et al.

(10) Patent No.: US 12,773,263 B2
(45) Date of Patent: Oct. 27, 2026

(54) BIPOLAR ABLATION GRAPHICAL USER INTERFACE

(71) Applicant: BIOSENSE WEBSTER (ISRAEL) LTD., Yokneam (IL)

(72) Inventors: Ella Ozeri, Binyamina (IL); Assaf Govari, Haifa (IL); Andres Claudio Altmann, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 1157 days.

(21) Appl. No.: 17/536,492

(22) Filed: Nov. 29, 2021

(65) Prior Publication Data

US 2022/0192742 A1 Jun. 23, 2022

Related U.S. Application Data

(60) Provisional application No. 63/128,878, filed on Dec. 22, 2020.

(51) Int. Cl.
*A61B 18/14* (2006.01)
*A61B 17/00* (2006.01)
*A61B 18/00* (2006.01)

(52) U.S. Cl.
CPC .............................. *A61B 18/1492* (2013.01); *A61B 2017/00199* (2013.01); *A61B 2018/0022* (2013.01);
(Continued)

(58) Field of Classification Search
CPC ...... A61B 18/1492; A61B 2017/00199; A61B 2018/0022; A61B 2018/00267;
(Continued)

(56) References Cited

U.S. PATENT DOCUMENTS 5,944,022 A 8/1999 Nardella
5,983,126 A 11/1999 Wittkampf
(Continued)

FOREIGN PATENT DOCUMENTS

CN 110944581 A 3/2020
EP 3206613 8/2017
(Continued)

OTHER PUBLICATIONS

Communication pursuant to Article 94(3) EPC received in EP application No. 21 216 312.5 dated Mar. 28, 2025.
(Continued)

*Primary Examiner* — Adam Z Minchella
(74) *Attorney, Agent, or Firm* — Clayton, McKay & Bailey, PC

(57) ABSTRACT

Methods, apparatuses, and computer program products implement embodiments of the present invention that include grouping a set of electrodes disposed at a distal end of a medical probe and configured to contact tissue in a body cavity into a plurality of groups of adjacent electrodes. A set of selectable widgets having a one-to-one correspondence with the groups are presented on a display, and in response to receiving an input indicating selection of a given widget, an ablation selection status of one or more of the electrodes in the group corresponding to the selected widget can be toggled.

18 Claims, 7 Drawing Sheets

(52) U.S. Cl.
CPC ............... *A61B 2018/00267* (2013.01); *A61B 2018/00351* (2013.01); *A61B 2018/00577* (2013.01); *A61B 2018/00613* (2013.01); *A61B 2018/141* (2013.01); *A61B 2018/1435* (2013.01); *A61B 2018/1467* (2013.01)

(58) Field of Classification Search
CPC ........... A61B 2018/00351; A61B 2018/00577; A61B 2018/00613; A61B 2018/141; A61B 2018/1435; A61B 2018/1467
See application file for complete search history.

(56) References Cited

U.S. PATENT DOCUMENTS

| | | | | |
|---|---|---|---|---|
| 6,456,864 | B1 | 9/2002 | Swanson | |
| 6,625,482 | B1 | 9/2003 | Panescu | |
| 9,844,406 | B2 | 12/2017 | Edwards | |
| 10,470,826 | B2 | 11/2019 | Brewster | |
| 10,864,039 | B2 | 12/2020 | Chan et al. | |
| 2008/0262489 | A1 | 10/2008 | Steinke | |
| 2014/0171942 | A1 | 6/2014 | Werneth | |
| 2014/0330266 | A1 | 11/2014 | Thompson et al. | |
| 2019/0030328 | A1* | 1/2019 | Stewart | A61B 18/1492 |
| 2019/0083169 | A1* | 3/2019 | Single | A61B 18/1492 |
| 2019/0175265 | A1 | 6/2019 | Govari | |
| 2020/0237425 | A1* | 7/2020 | Laughner | A61B 18/1492 |
| 2020/0297415 | A1* | 9/2020 | Marshik | A61B 90/361 |

FOREIGN PATENT DOCUMENTS

| | | | |
|---|---|---|---|
| JP | H10-033551 | | 2/1998 |
| JP | 2014533130 | A | 12/2014 |
| JP | 2019505308 | A | 2/2019 |
| WO | 2007024983 | A2 | 3/2007 |
| WO | WO2013052590 | | 4/2013 |
| WO | 2014179110 | A1 | 11/2014 |
| WO | 2020159903 | A1 | 8/2020 |

OTHER PUBLICATIONS

Extended European Search Report received in EP application No. 21 216 312.5 dated May 23, 2022.

Notification of Reasons for Refusal received in JP Patent Application 2021-206829 dated Jun. 17, 2025.

Office Action received in CN Application No. 202111579869.2 dated Mar. 26, 2026.

* cited by examiner

BIPOLAR ABLATION GRAPHICAL USER INTERFACE

CROSS-REFERENCE TO RELATED APPLICATIONS

This application claims the benefit of U.S. Provisional Patent Application 63/128,878, filed Dec. 22, 2020, which is incorporated herein by reference.

FIELD OF THE INVENTION

The present invention relates generally to tissue ablation procedures, and specifically to generating and presenting a graphical user interface that can be used to select ablation electrodes on an ablation catheter.

BACKGROUND OF THE INVENTION

Arrhythmias are abnormal heart rhythms that are typically caused by a small area of cardiac tissue that produces irregular heartbeats. Cardiac ablation is a medical procedure that can be performed to treat an arrhythmia by destroying the area of the cardiac tissue causing the irregular heartbeats. Some medical systems use irreversible electroporation (IRE) to ablate cardiac tissue. IRE is a nonthermal ablation method based on the unrecoverable permeabilization of cell membranes caused by short pulses of high voltage delivered to the tissue.

U.S. Patent Application 2014/0171942 to Werneth et al., describes a user interface for a tissue ablation system. The user interface can be used in conjunction with an ablation catheter that includes at least two ablation elements used to deliver energy to tissue. The user interface provides a visual representation of the geometry of the at least two ablation elements. The system may be programmable so that energy is delivered to certain electrodes or pairs of electrodes in a predetermined sequence or sequences determined and/or selected by an operator.

U.S. Pat. No. 9,844,406 to Edwards et al., describes a graphical user interface (GUI) for association with an electrode structure deployed in contact with a tissue region. When using this GUI, a physician can select or deselect individual electrodes using selection keys while in standby or ready modes. While the GUI typically prevents electrode selection/deselection while not delivering ablation energy to the electrodes, the GUI can be configured to allow electrode selection/deselection while delivering ablation energy.

U.S. Patent Application 2019/0175265 to Govari et al., describes a graphical user interface (GUI) for displaying estimated cardiac catheter proximity to the esophagus. The GUI displays the arrangement of catheter electrodes 40 in the form of a diagram. In one embodiment, the GUI displays the arrangement of the electrodes relative to esophagus tissue by presenting a diagram that indicates the respective distances of the electrodes to a marked location on the esophagus tissue.

U.S. Pat. No. 10,470,826 to Brewster et al., describes systems and methods for selecting, activating, or selecting and activating transducers. The system includes a transducer-based device that assumes an unexpanded configuration for delivery to the left atrium, and that is expanded upon being deployed within the left atrium so as to enable a plurality of transducers proximate to engage tissue of the left atrium. The system also includes a graphical user interface that presents respective transducer graphical elements corresponding to transducers on the device, and that enables selection of the transducers.

U.S. Pat. No. 6,625,482 to Panescu et al., describes a graphical user interface (GUI) for use with multiple electrode catheters. The GUI generates and displays an image of the multiple electrode catheter, and can present highlighted symbols that indicate early activation sites adjacent to specific electrodes.

SUMMARY OF THE INVENTION

There is provided, in accordance with an embodiment of the present invention, a method including grouping a set of electrodes disposed at a distal end of a medical probe and configured to contact tissue in a body cavity into a plurality of groups of adjacent electrodes, presenting, on a display, a set of selectable widgets having a one-to-one correspondence with the groups, receiving, by a processor, an input indicating selection of a given widget, and toggling, in response to the selection, an ablation selection status of one or more of the electrodes in the group corresponding to the selected widget.

In one embodiment, the groups include overlapping groups of the electrodes.

In another embodiment, the method further includes identifying the ablation selection status for each of the electrodes, presenting, on the display, a set of icons having a one-to-one correspondence with the electrodes, wherein the presented icons include respective visual configurations of the ablation selection status of the electrodes.

In an additional embodiment, the distal end is selected from a group consisting of a lasso, a basket, a balloon, and a deflectable element.

In a further embodiment, the method further includes identifying a toggle status for each of the groups, wherein the toggle status for a given group indicates whether or not the ablation selection status of any of the electrodes in the given group can be toggled between a selectable and a non-selectable state, wherein the presented widgets include respective visual configurations of the toggle status of the widgets, and wherein receiving the toggle status of the given widget indicates that the ablation selection status of the electrodes in the corresponding group can be toggled.

In a supplemental embodiment, the method supplementally includes presenting a toggle widget on the display, and wherein upon receiving an input selecting the toggle widget, setting the ablation selection status to the plurality of electrodes to the selectable state.

In one embodiment, the method further includes presenting a toggle widget on the display, and wherein upon receiving an input selecting the toggle widget, setting the ablation selection status to the plurality of electrodes to the non-selectable state.

In another embodiment, the electrodes include ablation electrodes, and the method further includes conveying ablation energy to the ablation electrodes having selectable states.

In an additional, wherein the ablation energy includes irreversible electroporation.

In a further embodiment, selecting the given widget toggles the given widget between a widget selected state and a widget deselected state.

In some embodiments, wherein upon toggling the selected widget from a widget deselected state to a widget selected state in response to the input and detecting that the ablation selection status of the electrodes adjacent to the electrodes in the group corresponding to the selected widget are non-selected, setting the ablation selection status of the electrodes in the corresponding group to selected.

In other embodiments, each of the groups include a pair of outer electrodes encompassing one or more inner electrodes, and wherein upon toggling the selected widget from a widget deselected state to a widget selected state in response to the input and detecting that the ablation selection status of the electrodes adjacent to the electrodes in the group corresponding to the selected widget are selected, setting the ablation selection status of the one or more inner electrodes in the corresponding group to selected.

In additional embodiments, each of the groups include a pair of outer electrodes encompassing one or more inner electrodes, and wherein upon toggling the selected widget from a widget deselected state to a widget selected state in response to the input, detecting that the ablation selection status a first given electrode adjacent to the electrodes in the group corresponding to the selected widget is selected, and detecting that the ablation selection status a first given electrode adjacent to the electrodes in the corresponding group is non-selected, setting the ablation selection status of the outer electrode adjacent to first given electrode to selected.

In further embodiments, wherein upon toggling the selected widget from a widget selected state to a widget deselected state in response to the input and detecting that the ablation selection status of the electrodes adjacent to the electrodes in the group corresponding to the selected widget are non-selected, setting the ablation selection status of the electrodes in the corresponding group to deselected.

In supplemental embodiments, each of the groups include a pair of outer electrodes encompassing one or more inner electrodes, and wherein upon toggling the selected widget from a widget selected state to a widget deselected state in response to the input and detecting that the ablation selection status of the electrodes adjacent to the electrodes in the group corresponding to the selected widget are selected, setting the ablation selection status of the one or more inner electrodes in the corresponding group to deselected.

In additional embodiments, each of the groups include a pair of outer electrodes encompassing one or more inner electrodes, and wherein upon toggling the selected widget from a widget selected state to a widget deselected state in response to the input, detecting that the ablation selection status a first given electrode adjacent to the electrodes in the group corresponding to the selected widget is selected, and detecting that the ablation selection status a first given electrode adjacent to the electrodes in the corresponding group is non-selected, setting the ablation selection status of the outer electrode adjacent to first given electrode to deselected.

There is also provided, in accordance with an embodiment of the present invention, an apparatus including an invasive medical probe configured to be inserted into a body cavity and including a set of electrodes disposed at a distal end of the probe and configured to contact tissue in the body cavity, a display, and a processor configured to group the set of electrodes into a plurality of groups of adjacent electrodes, to presenting, on the display, a set of selectable widgets having a one-to-one correspondence with the groups, to receive an input indicating selection of a given widget, and to toggle, in response to the selection, an ablation selection status of one or more of the electrodes in the group corresponding to the selected widget.

There is additionally provided, in accordance with an embodiment of the present invention, a computer software product, operated in conjunction with a medical probe configured to be inserted into a body cavity and including a set of electrodes disposed at a distal end of the probe and configured to contact tissue in the body cavity, the product including a non-transitory computer-readable medium, in which program instructions are stored, which instructions, when read by a computer, cause the computer to group the set of electrodes into a plurality of groups of adjacent electrodes, to present, on a display, a set of selectable widgets having a one-to-one correspondence with the groups, to receive an input indicating selection of a given widget; and to toggle, in response to the selection, an ablation selection status of one or more of the electrodes in the group corresponding to the selected widget.

BRIEF DESCRIPTION OF THE DRAWINGS

The disclosure is herein described, by way of example only, with reference to the accompanying drawings, wherein.

DETAILED DESCRIPTION OF EMBODIMENTS

During an irreversible electroporation (IRE) bipolar ablation procedure, an operator typically desires to ablate a selected region in proximity to electrodes of a catheter. However, when using multi-electrode circular catheters (e.g., lasso catheters, small basket catheters, and small balloon catheters), there are limitations on the electrodes that can be efficiently used.

Embodiments of the present invention provide methods and systems for providing a graphical user interface (GUI) for selecting electrodes of a multi-electrode catheter. As described hereinbelow, a set of electrodes disposed at a distal end of a medical probe and configured to contact tissue in a body cavity are grouped into a plurality of groups of adjacent electrodes, and a set of selectable widgets having a one-to-one correspondence with the groups are presented on a display. Upon receiving an input indicating selection of a given widget, an ablation selection status of one or more of the electrodes in the group corresponding to the selected widget can be toggled in response to the selection.

In some embodiments, the widgets may be presented with a visual configuration that indicates respective toggle statuses for the groups, wherein the toggle status for a given group indicates whether or not the ablation selection status of any of the electrodes in the given group can be toggled between a selectable and a non-selectable state. In these embodiments, a first given widget having a selectable state corresponds to a first given group of electrodes whose ablation selection status can be toggled, and a second given widget having a non-selectable state corresponds to a second given group of electrodes whose ablation selection status cannot be toggled. Systems implementing embodiments of the present invention can configure the toggle statuses of the widgets so as to prevent any gaps in the electrodes selected for ablation, thereby balancing (i.e., evening out) delivery of ablation energy from the electrodes to body cavity tissue.

System Description

Figure 1:
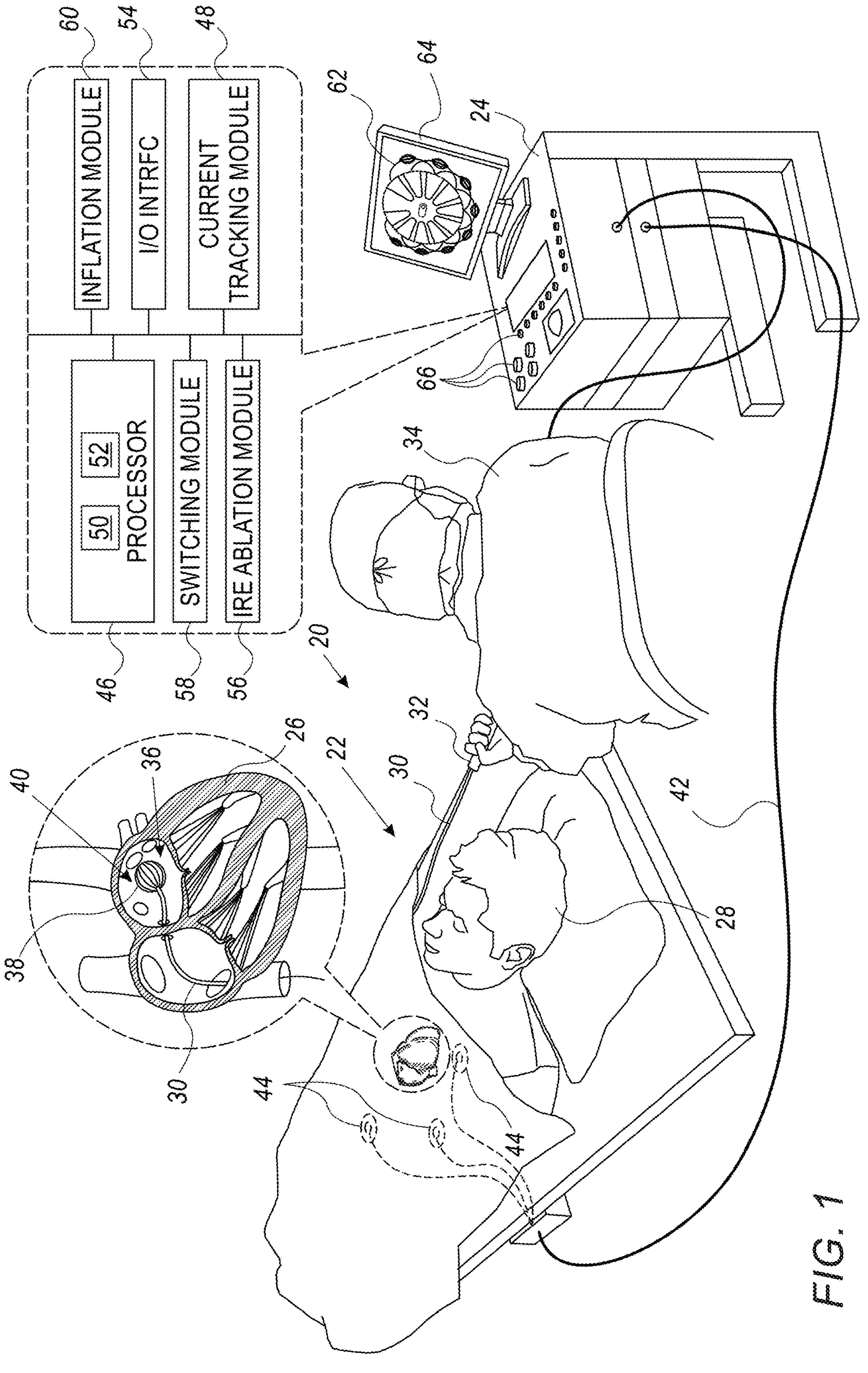
FIG. 1 is a schematic, pictorial illustration of a medical system comprising a multi-electrode medical probe and a control console configured to present a graphical user interface (GUI) for selecting and deselecting groups of electrodes, in accordance with an embodiment of the present invention.

FIG. 1 is a schematic, pictorial illustration of a medical system 20 comprising an invasive medical probe 22 and a control console 24, in accordance with an embodiment of the present invention. Medical system 20 may be based, for example, on the CARTO® system, produced by Biosense Webster Inc. of 33 Technology Drive, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Probe 22 comprises an insertion tube 30 and a handle 32 coupled to a proximal end of the insertion tube. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy an electrode assembly 38 affixed to distal end 26. Electrode assembly 38 comprises a set of electrodes arranged in a circular configuration, as described in the descriptions referencing FIGS. 2 and 4 hereinbelow.

To start performing a medical procedure such as irreversible electroporation (IRE) ablation, medical professional 34 can manipulate handle 32 to position distal end 36 so that electrodes 40 engage cardiac tissue at a desired location or locations. In some embodiments, electrode assembly 38 may comprise a balloon-shaped electrode assembly as described in the description referencing FIG. 2 hereinbelow, or a lasso-shaped electrode assembly as described in FIG. 4 hereinbelow. While embodiments described herein describe using a balloon electrode assembly or a lasso electrode assembly, other configurations of electrode assembly 38 are considered to be within the spirit and scope of the present invention. In one example, electrode assembly 38 may comprise a basket-shaped electrode assembly. In another example, electrode assembly 38 may comprise a set of electrodes 40 affixed to a deflectable tip element of distal end 36.

In the configuration shown in FIG. 1, control console 24 is connected, by a cable 42, to body surface electrodes, which typically comprise adhesive skin patches 44 that are affixed to patient 28. Control console 24 comprises a processor 46 that, in conjunction with a current tracking module 48, determines location coordinates of distal end 36 inside heart 26 based on impedances and/or currents measured between adhesive skin patches 44 and electrodes 40 that are affixed to electrode assembly 38. In addition to being used as location sensors during a medical procedure, electrodes 48 may perform other tasks such as ablating tissue in the heart.

As described hereinabove, in conjunction with current tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. In embodiments of the present invention, electrodes 40 are also configured to apply IRE ablation energy to tissue in heart 26.

Processor 46 may comprise real-time noise reduction circuitry 50 typically configured as a field programmable gate array (FPGA), followed by an analog-to-digital (A/D) signal conversion integrated circuit 52. The processor can be programmed to perform one or more algorithms disclosed herein, each of the one or more algorithms comprising steps described hereinbelow. The processor uses circuitry 50 and circuit 52 as well as features of modules which are described in more detail below, in order to perform the one or more algorithms.

Although the medical system shown in FIG. 1 uses impedance or current-based sensing to measure a location of distal end 36, other location tracking techniques may be used (e.g., techniques using magnetic-based sensors). Impedance and current-based location tracking techniques are described, for example, in U.S. Pat. Nos. 5,983,126, 6,456,864 and 5,944,022. The methods of location sensing described hereinabove are implemented in the above-mentioned CARTO® system and are described in detail in the patents cited above.

Control console 24 also comprises an input/output (I/O) communications interface 54 that enables control console 24 to transfer signals from, and/or transfer signals to electrodes 40 and adhesive skin patches 44. In the configuration shown in FIG. 1, control console 24 additionally comprises an IRE ablation module 56 and a switching module 58.

IRE ablation module 56 is configured to generate IRE pulses comprising peak power in the range of tens of kilowatts. As described hereinbelow, medical system 20 performs IRE ablation by delivering IRE pulses to pairs of electrodes 40. Using switching module 58, IRE ablation module 56 can deliver one or more IRE pulses independently to each of the pairs of the electrodes.

In one embodiment as described supra, electrode assembly 38 may comprise a balloon. In this embodiment, control console 24 further comprise an inflation module 60, which is described in the description referencing FIG. 2 hereinbelow.

In embodiments described herein, processor 46 executes and presents a graphical user interface (GUI) 62 on a display 64. As described hereinbelow, medical professional 34 can use GUI 62 to select groupings of electrodes that are to be used to deliver IRE ablation energy to tissue in heart 26. In some embodiments, medical professional 34 can interact with GUI 62 using one or more input devices 62. In alternative embodiments, display 64 may comprise a touchscreen that can be configured to accept inputs from medical professional 34, in addition to presenting GUI 62.

Figure 2:
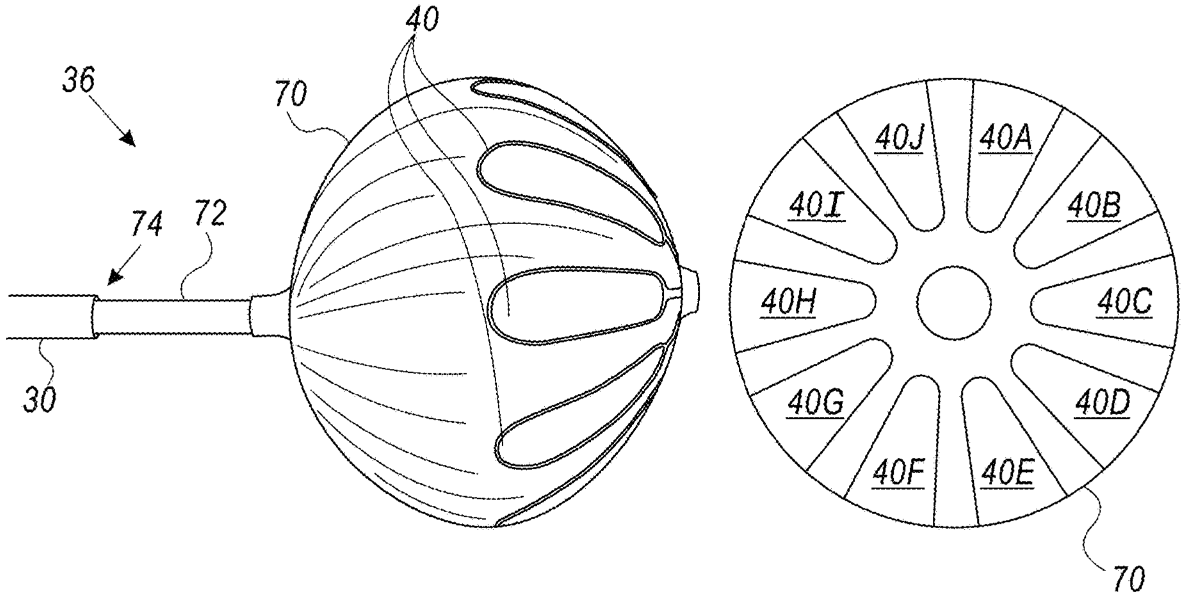
FIG. 2 is a schematic pictorial illustration of a first example of a distal end of a multi-electrode balloon medical probe, in accordance with an embodiment of the present invention.

FIG. 2 is a schematic pictorial illustration of electrode assembly 38 in accordance with a first electrode assembly embodiment of the present invention. In the configuration shown in FIG. 2, electrodes 40 are attached to an exterior wall of a balloon 70. Balloon 70 is affixed to a tubular shaft 72 that is configured to extend from a distal end of a lumen 74 of insertion tube 30, and the balloon is configured to be deployed through the lumen into a body cavity such as heart 26. To inflate balloon 70, inflation module 60 can pump, via an inflation lumen (not shown) contained in shaft 72, a fluid (e.g., normal saline) into the balloon.

Balloon 70 is typically formed from bio-compatible material such as polyethylene terephthalate (PET), polyurethane, Nylon, or Pebax. A first set of electrodes 40 can be fabricated with the balloon and typically comprise gold overlaying the exterior wall of the balloon. For simplicity, connections of electrodes 40 to interface 54 and modules 56 and 58 are not shown. In FIG. 2, electrodes 40 in the first set can be differentiated by appending a letter to the identifying numeral, so that the electrodes comprise electrodes 40A-40J.

Figure 3:
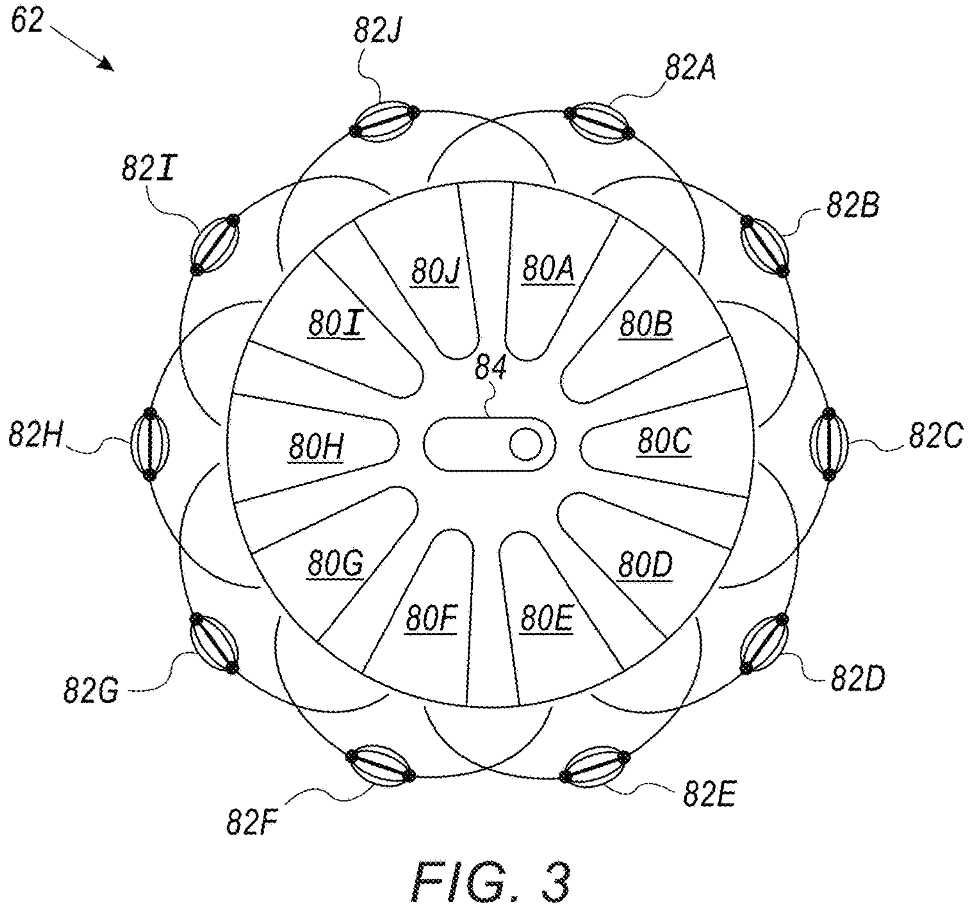
FIG. 3 is a schematic pictorial illustration of a GUI that can be used to select and deselect electrodes in the first example of the multi-electrode balloon medical probe, in accordance with an embodiment of the present invention.

FIG. 3 is a schematic pictorial illustration of GUI 62, in accordance with a first GUI embodiment of the present invention. In the first GUI embodiment, GUI 62 comprises a first set of electrode icons 80 that have a one-to-one correspondence with the first set of electrodes 40 attached to balloon 70, a first set of triplet selection widgets 82 and a toggle widget 84.

In FIG. 3 (and in FIGS. 14 and 15 that are described hereinbelow), icons 80 and selectable widgets 82 can be differentiated by appending a letter to the identifying numeral, so that the electrode icons comprise icons 80A-80J and the group selection widgets comprise widgets 82A-82J.

Typically, medical system 20 is constrained to use specific groupings of electrodes 40 to perform an IRE ablation operation on tissue in a body cavity of patient 28. In embodiments described herein, the constraint is that medical system 20 uses triplets of electrodes. For example, if a given triplet comprises the electrodes corresponding to icons 80A, 80B and 80C, then the medical system 20 performs bipolar ablation sequentially using the following pairs of electrodes:

The electrodes corresponding to icons 80A and 80B.

The electrodes corresponding to icons 80B and 80C.

The electrodes corresponding to icons 80A and 80C.

While using medical system 20, medical professional 34 can interact with GUI 62 (e.g., using input devices 66 or touchscreen 64) to select a given widget 82, and in response to selecting the given widget, processor 46 can select/deselect a respective triplet of electrode icons 80 (and thereby select/deselect their corresponding electrodes 40 for IRE ablation) per the following table:

| Widget | Triplet |
|---|---|
| 82A | 80J, 80A, 80B |
| 82B | 80A, 80B, 80C |
| 82C | 80B, 80C, 80D |
| 82D | 80C, 80D, 80E |
| 82E | 80D, 80E, 80F |
| 82F | 80E, 80F, 80G |
| 82G | 80F, 80G, 80H |
| 82H | 80G, 80H, 80I |

-continued

| Widget | Triplet |
|---|---|
| 82I | 80H, 80I, 80J |
| 82J | 80I, 80J, 80A |

In GUI 62, toggle widget 84 is similar to an on/off switch in that in response to medical professional 34 selecting the toggle widget, processor 46 selects/deselects all icons 82 presented by the GUI in FIG. 3 (i.e., icons 80A-80J).

While embodiments herein describe the electrode selections in the form of triplets, using other groupings of electrodes 40 is considered to be within the spirit and scope of the present invention. For example, electrodes 40 may be selected using quad groupings (e.g., a grouping of electrodes 40 corresponding to icons 80A, 80B, 80C and 80D).

Figure 4:
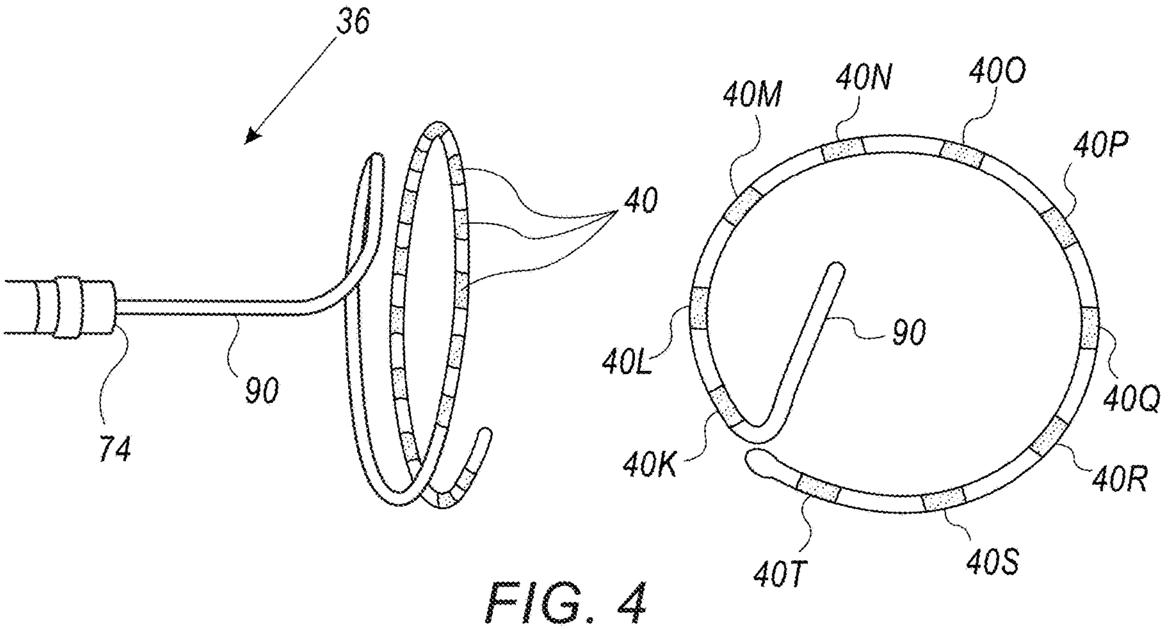
FIG. 4 is a schematic pictorial illustration of a second example of a distal end of a multi-electrode lasso medical probe, in accordance with an embodiment of the present invention.

FIG. 4 is a schematic pictorial illustration of electrode assembly 38, in accordance with a second electrode assembly embodiment of the present invention. In the configuration shown in FIG. 4, electrode assembly 38 comprises a second set of electrodes 40 that are affixed to an end section 90 that is formed as a complete or partial lasso, i.e., as a preformed arcuate structure. In FIG. 4, electrodes 40 in the second set can be differentiated by appending a letter to the identifying numeral, so that the electrodes comprise electrodes 40K-40T.

In embodiments described herein, end section 90 may also be referred to as lasso 90. The arcuate and possibly helical shape of end section 90 may be maintained, for example, by incorporating a thin strut made from a shape memory material, such as Nitinol (not shown), in the desired shape within the end section. The strut is made sufficiently flexible to permit the end section to straighten during insertion and withdrawal through lumen 74, but to resume its arcuate form when it is unconstrained inside the heart chamber. The second set of electrodes 40 are connected to control console 24 by wires (not shown) running through medical probe 22.

Figure 5:
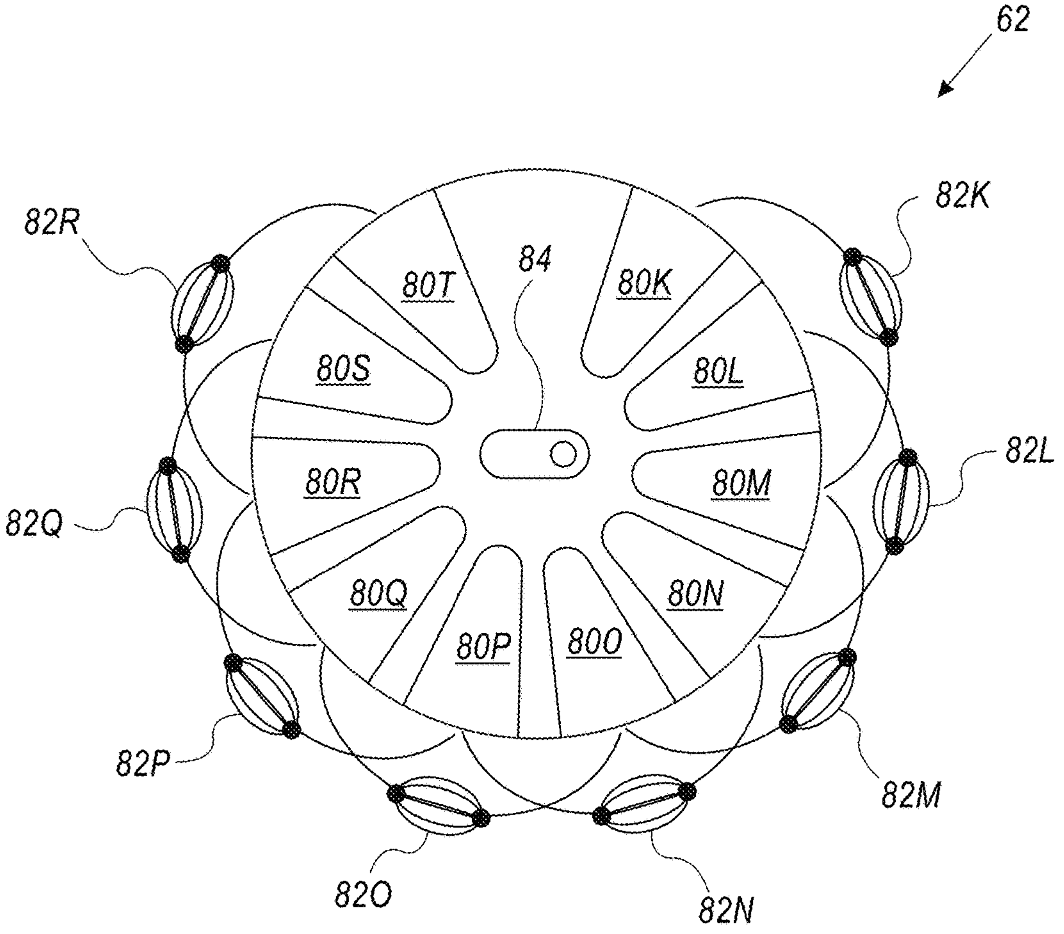
FIG. 5 is a schematic pictorial illustration of a GUI that can be used to select and deselect electrodes in the second example of the multi-electrode lasso medical probe, in accordance with an embodiment of the present invention.

FIG. 5 is a schematic pictorial illustration of GUI 62, in accordance with a second GUI embodiment of the present invention. In the second GUI embodiment, GUI 62 comprises a second set of electrode icons 80 that have a one-to-one correspondence with the second set of electrodes 40 attached to lasso 90, a second set of group selection widgets 82 and toggle widget 84.

In FIG. 5 (and in FIGS. 8-13 that are described hereinbelow), icons 80 and widgets 82 can be differentiated by appending a letter to the identifying numeral, so that the electrode icons comprise icons 80K-80T, and the group selection widgets comprise widgets 82K-82R.

While using medical system 20, medical professional 34 can interact with GUI 62 (e.g., using input devices 66 or touchscreen 64) to select a given widget 82, and in response to selecting the given widget, processor 46 can select/deselect a triplet of electrode icons 80 (and thereby select/deselect their corresponding electrodes 40 for IRE ablation) per the following table:

| Widget | Triplet |
|---|---|
| 82K | 80K, 80L, 80M |
| 82L | 80L, 80M, 80N |
| 82M | 80M, 80N, 80O |
| 82N | 80N, 80O, 80P |
| 82O | 80O, 80P, 80Q |

-continued

| Widget | Triplet |
|---|---|
| 82P | 80P, 80Q, 80R |
| 82Q | 80Q, 80R, 80S |
| 82R | 80R, 80S, 80T |

Figure 6:
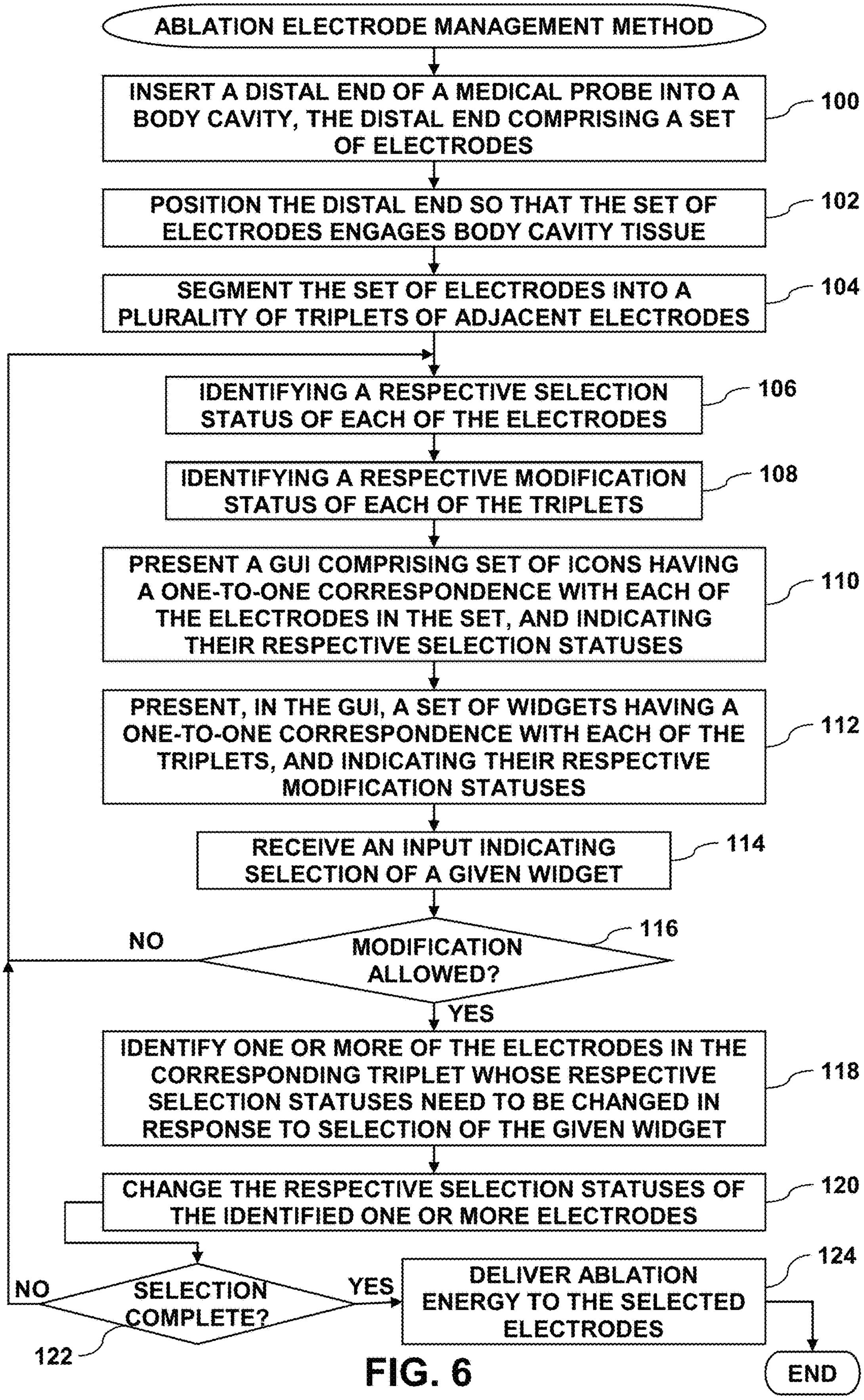
FIG. 6 is a flow diagram that schematically illustrates a method for using the GUI to select and deselect electrodes of a multi-electrode medical probe, in accordance with an embodiment of the present invention.

FIG. 6 is a flow diagram that schematically illustrates a method of using GUI 62 to select and deselect triplets of adjacent electrode icons, in accordance with an embodiment of the present invention. In an insertion step 100, medical professional 34 inserts distal end 36 of medical probe 22 into a body cavity (e.g., a chamber of heart 26) of patient 28, and in an engaging step 102, the medical professional manipulates handle 32 so that electrode assembly 38 engages tissue in the body cavity.

In a grouping step 104, processor 46 partitions electrodes 40 into a plurality of overlapping groups of adjacent electrodes 40. While the examples described herein describe groups comprising triplets that correspond to widgets 82A-82R, groups comprising any plurality of electrodes 40 (e.g., two, four or five) are considered to be within the spirit and scope of the present invention.

In a first identification step 106, processor 46 identifies a respective ablation selection status (i.e., selected or not selected) of each electrode 40. In embodiments described herein, the ablation selection status for a given electrode 40 may comprise a selected state or a non-selected state, and ablation module 56 and switching module 58 deliver IRE ablation energy only to the electrodes that are selected (i.e., have selected states).

In a second identification step 108, processor 46 identifies a respective toggle status for each of the widgets corresponding to respective sets (e.g., triplets) of electrodes 40. In embodiments herein, the toggle status of a given group is indicated by the toggle status of its corresponding widget 82. Toggle statuses are described in the description referencing FIG. 7 hereinbelow.

As described supra, medical system 20 is constrained to use specific groupings of electrodes 40 to perform an IRE ablation operation on tissue in a body cavity of patient 28. In embodiments described herein, each of the groupings comprises a triplet of electrodes 40. However, if medical professional 34 selects some triplets of electrodes 40, then this may cause problems in the ablation.

For example, medical professional 34 may select a first triplet comprising electrodes 40B, 40C and 40D, and a second triplet comprising electrodes 40E, 40F and 40G. Even though these triplets include electrodes 40B-40G, the region of tissue between adjacent electrodes 40D and 40E is not covered (i.e., by the selected triplets). In some embodiments, processor 46 can prevent this selection (i.e., of triplets 40B, 40C, 40D and 40E, 40F, 40G) to prevent any ambiguity about whether or not the region of tissue between adjacent electrodes 40D and 40E will be ablated. In this example (i.e., of selecting triplets 40B, 40C, 40D and 40E, 40F, 40G), even though electrodes 40B-40G are selected, the region of tissue between adjacent electrodes 40D and 40E will not ablated since none of the selected triplets include the pair of electrodes 40D and 40E. An example of having a gap in an ablation procedure is described in the description referencing FIG. 15 hereinbelow.

In a first embodiment, GUI 62 can prevent medical professional 34 from selecting the second triplet (i.e., to prevent forming the gap between electrodes 40D and 40E). In a second embodiment, GUI 62 accepts the selection of the first and second triplets, detects that the region between electrodes 40D and 40E is not covered, and automatically selects further triplets of electrodes 40C, 40D, 40E and electrodes 40D, 40E, 40F to cover the gap between electrodes 40D and 40E. In this embodiment, GUI 62 can reflect these automatically selected triplets, as described in the description referencing FIG. 15 hereinbelow. GUI 62 automatically selecting triplets 40C, 40D, 40E and 40D, 40E, 40F ensures that medical system 20 can deliver an even amount of ablation energy to the region of tissue encompassed by electrodes 40B and 40G.

Figure 7:
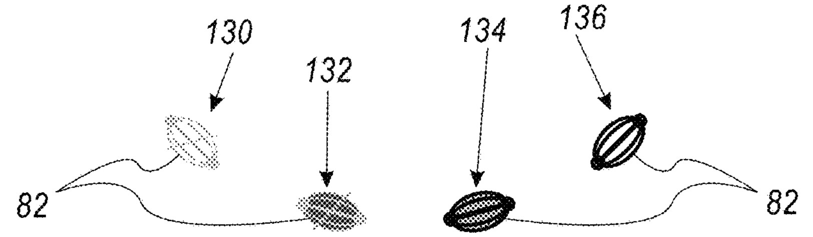
FIG. 7 is a schematic pictorial illustration of examples of widgets that the GUI can present for selecting and deselecting groups of the electrodes, in accordance with an embodiment of the present invention.

FIG. 7 is a schematic pictorial illustration that shows examples of visual configurations 130-136 of widgets 82 that GUI 62 can use to indicate a toggle status of a corresponding triplet of electrodes 40, in accordance with an embodiment of the present invention. In embodiments described herein, the toggle status for a given triplet of electrodes 40 indicates whether or not the given triplets are selected or deselected, and whether or not the ablation selection status of the triplet electrodes can be changed. In the examples shown in FIG. 7:

A given widget 82 comprising visual configuration 130 indicates that the electrodes in the corresponding triplet are currently not selected and cannot be selected.

A given widget 82 comprising visual configuration 132 indicates that the electrodes in the corresponding triplet are currently not selected but can be selected.

A given widget 82 comprising visual configuration 134 indicates that the electrodes in the corresponding triplet are currently selected and can be deselected.

A given widget 82 comprising visual configuration 136 indicates that the electrodes in the corresponding triplet are currently selected but cannot be deselected.

In some embodiments, the toggle status of a given group indicates whether or not the group can be selected/deselected. In these embodiments, the toggle status of a given group referenced by a given widget 82 comprising visual configurations 132 and 134 is selectable (i.e., the group can be selected/deselected), and a given group referenced by a given widget 82 comprising visual configurations 130 and 136 is non-selectable (i.e., the group cannot be selected/deselected).

Returning to the flow diagram, in a first presentation step 110, processor 46 presents GUI 62 comprising a set of icons 80 having a one-to-one correspondence to electrodes 40 and that indicate their respective ablation selection statuses. As described supra, the ablation selection status for a given electrode 40 indicates whether or not the given electrode is selected.

In some embodiments, GUI 62 can present icons 80 using visual configurations indicating their respective ablation selection statuses. In the examples described in the description referencing FIGS. 8-15 hereinbelow, if a given electrode 40 is selected, then GUI 62 presents the corresponding icon 80 with shading, and if a given electrode 40 is not selected, then the GUI presents the corresponding icon 80 without shading.

In a second presentation step 112, processor 45 presents, in GUI 62, a set of widgets 82 having a one-to-one correspondence to the defined triplets of electrodes 40 and that indicate their respective toggle statuses. As described supra in the description referencing FIG. 7, the toggle status for a given triplet of electrodes 40 indicates whether or not the given triplet is selected and can be deselected, selected but cannot be deselected, not selected but can be selected, or not selected and cannot be selected.

FIGS. 8-15 are examples of how GUI 62 can present icons 80 and widgets 82, in accordance with an embodiment of the present invention. GUI 62 in FIGS. 8-13 can be used to control the electrode assembly described in the description referencing FIGS. 4 and 5 hereinabove, and the GUI in FIGS. 14 and 15 can be used to control the electrode assembly described in the description referencing FIGS. 2 and 3 hereinabove.

Figure 8:
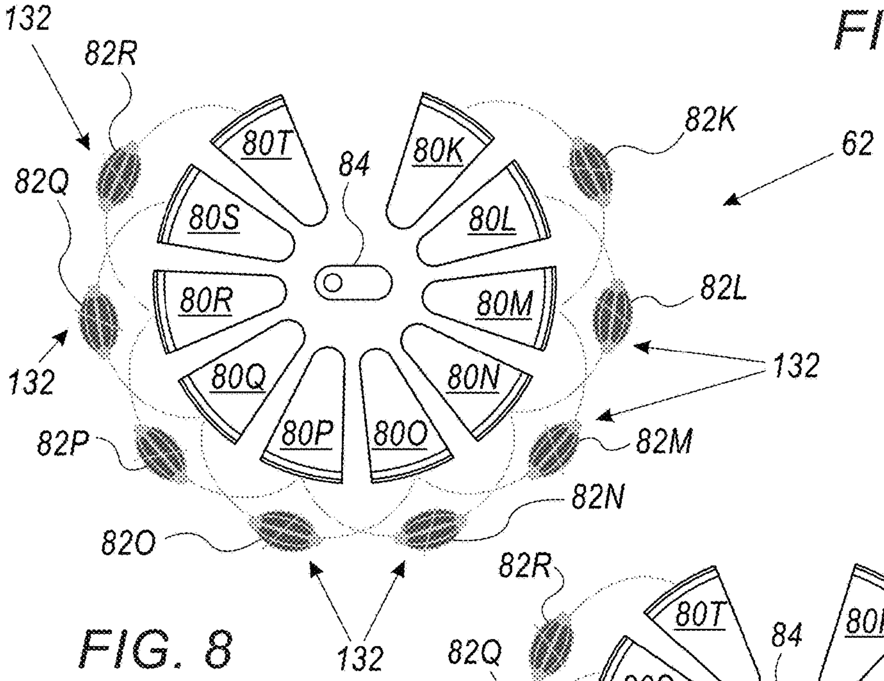
FIGS. 8-15 are schematic pictorial illustrations of examples of the GUI for selecting and deselecting the groups of the electrodes, in accordance with embodiments of the present invention.

In the example presented in FIG. 8, GUI 62 presents all widgets 82 using visual configuration 132, thereby indicating that no electrodes 40 are currently selected for ablation. Therefore, GUI 62 presents all icons 80 without shading.

Figure 9:
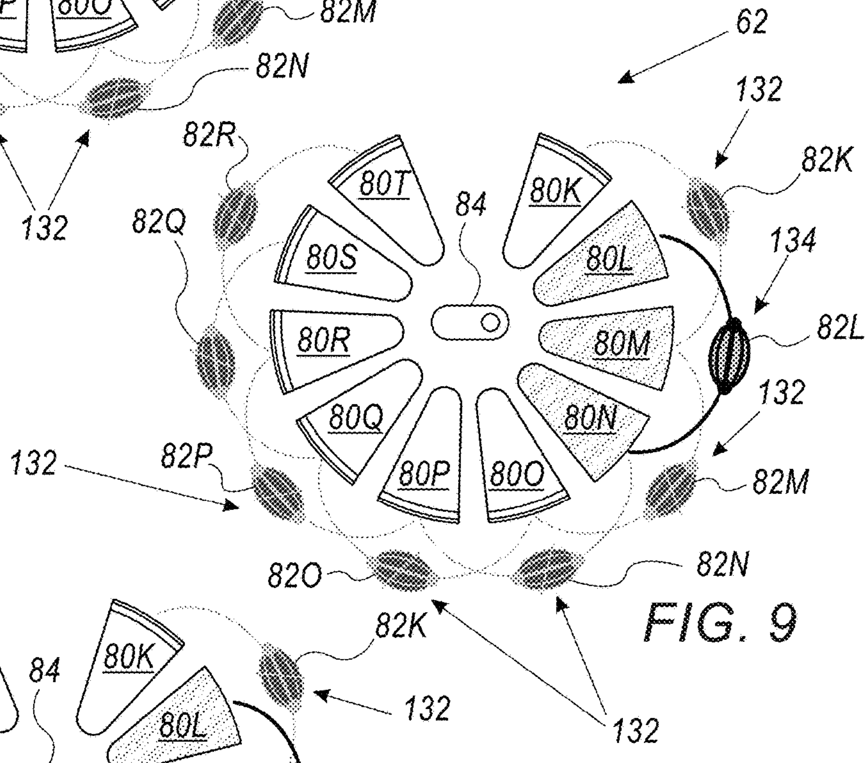

In the example presented in FIG. 9, in response to medical professional 34 clicking on widget 82L, processor 46 selects electrodes 40 corresponding to icons 80L-80N. In this example, GUI 62 presents widget 82L using visual configuration 134 and icons 80L-80N with shading indicating that electrodes 40L-40N are selected for ablation. The example presented in FIG. 9 can immediately follow the example presented in FIG. 8.

In the example presented in FIG. 9:

- The group of electrodes corresponding to (i.e., referenced by) widget 82L comprises 40L, 40M and 40N, respectively referenced by icons 80L, 80M and 80N.
- Electrodes 40 adjacent to this group (i.e. electrodes 40L, 40M and 40N) comprise electrodes 40K and 40O, respectively referenced by icons 80K and 80O.
- In this group, electrodes 40L and 40N may be referenced herein as outer ablation electrodes 40, and electrode 40M may be referenced herein as inner electrode 40M, as electrode 40M is encompassed by electrodes 40L and 40N
- As described supra, each the groups may comprise four or more electrodes 40. In these embodiments, if a given group comprises electrodes 40P, 40Q, 40R and 40S, then the outer electrodes comprise electrodes 40P and 40S, and the inner electrodes comprise electrodes 40Q and 40R. In other words, the inner electrodes may comprise one or more electrodes 40.

The examples presented in FIGS. 8 and 9 hereinabove, and FIGS. 10-15 hereinbelow can be based on the following sets of rules for a given widget 82 corresponding to a given group of three or more adjacent electrodes 40:

- In embodiments where in response to an input from a given input device 66, processor 46 changes the visual configuration of the given widget from visual configuration 132 to visual configuration 134 or 136:
  - If processor 46 detects that the ablation selection status of both of electrodes 40 adjacent to the group is "not selected", then the processor can change the ablation selection status of the electrodes in the group to "selected".
  - If processor 46 detects that the ablation selection status of both of electrodes 40 adjacent to the group is "selected", then the processor can change the ablation selection status of the one or more inner electrodes in the group to "selected".
  - If processor 46 detects that the ablation selection status of only one of the outer electrodes in the group is "not selected" (i.e., the ablation selection status of the other outer electrode in the group is "selected"), then the processor can change the ablation selection status of the only one of the electrodes to "selected".
- In embodiments where in response to an input from a given input device 66, processor 46 changes the visual configuration of the given widget from visual configuration 134 to visual configuration 130 or 132:
  - If processor 46 detects that the ablation selection status of both of electrodes 40 adjacent to the group is "selected", then the processor can change the ablation selection status of the electrodes in the group to "not selected".
  - If processor 46 detects that the ablation selection status of both of electrodes 40 adjacent to the group is "selected", then the processor can change the ablation selection status of the one or more inner electrodes in the group to "not selected".
  - If processor 46 detects that the ablation selection status of only one of the outer electrodes in the group is "selected" (i.e., the ablation selection status of the other outer electrode in the group is "not selected"), then the processor can change the ablation selection status of the only one of the electrodes to "not selected".

Note that rules described hereinabove that result in processor 46 changing the ablation selection status of the "inner" electrodes only apply to embodiments where the groups comprise three or more electrodes 40.

Figure 10:
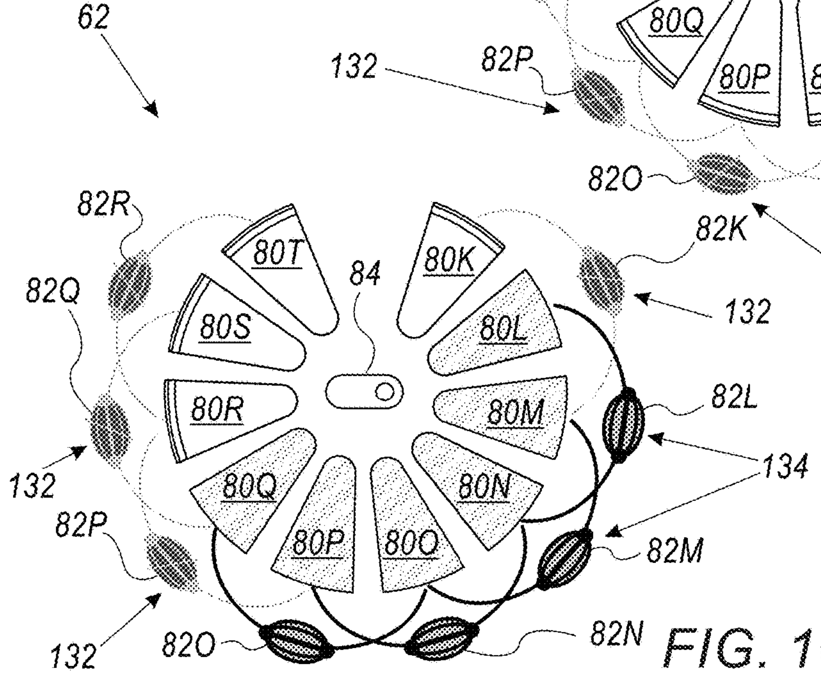

In the example presented in FIG. 10, in response to medical professional 34 clicking on widgets 82L, 82M, 82N and 82O, processor 46 selects electrodes 40 corresponding to icons 80L-80Q. In this example, GUI 62 presents widgets 82L-82O using visual configuration 134 and icons 80L-80Q with shading indicating that electrodes 40L-40Q are selected for ablation. In some embodiments as described supra, medical professional 34 can select the electrodes corresponding to icons 80L-80Q by selecting widgets 82L and 82O, and GUI 62 automatically "fills in" (i.e. by selecting) widgets 82M and 82N. The example presented in FIG. 10 can immediately follow the example presented in FIG. 9.

Figure 11:
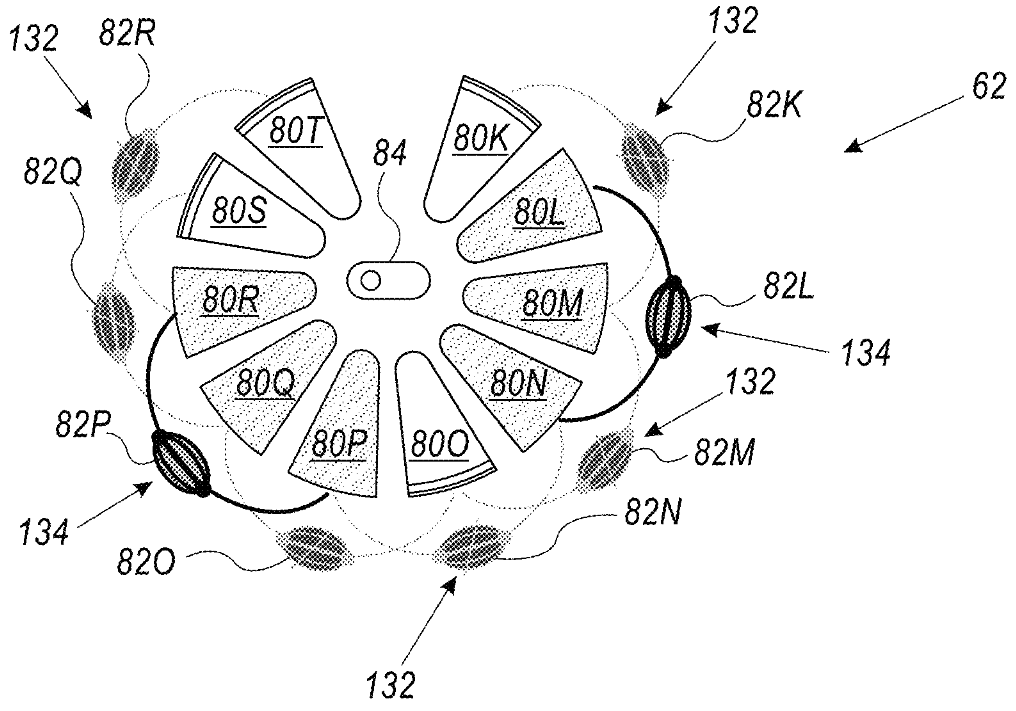

In the example presented in FIG. 11, in response to medical professional 34 clicking on widgets 82L and 82P, processor 46 selects electrodes 40 corresponding to icons 80L-80N and 80P-80R. In this example, GUI 62 presents widgets 82L and 82P using visual configuration 134 and icons 80L-80N and 80P-80R with shading indicating that electrodes 40L-40N and electrodes 40P-40R are selected for ablation.

In a first embodiment, the example presented in FIG. 11 can immediately follow the example presented in FIG. 9. In this embodiment, GUI 62 can transition from the configuration presented in FIG. 9 to the configuration presented in FIG. 11 in response to medical professional 34 clicking on (i.e., selecting) widget 82P.

In a second embodiment, the example presented in FIG. 11 can immediately follow the example presented in FIG. 10. In this embodiment, GUI 62 can transition from the configuration presented in FIG. 10 to the configuration presented in FIG. 11 in response to medical professional 34 clicking on the following sequence of widgets 82:

- Widget 82O. In FIG. 10, GUI 62 presents widget 82O using visual configuration 134, indicating that triplet of electrodes 40O, 40P and 40Q is selected. In response to medical professional 34 clicking on widget 82O, GUI 62 can deselect electrode 40Q, and present widget 82O using visual configuration 132 as shown in FIG. 11.
- Widget 82N. In FIG. 10, GUI 62 presents widget 82N using visual configuration 134, indicating that triplet of electrodes 40N, 40O and 40P is selected. In response to medical professional 34 clicking on widget 82N, GUI 62 can deselect electrode 40P and present widget 82N using visual configuration 132 as shown in FIG. 11.
- Widget 82M. In FIG. 10, GUI 62 presents widget 82M using visual configuration 134, indicating that triplet of electrodes 40M, 40N and 40O is selected. In response to medical professional 34 clicking on widget 82M, GUI 62 can deselect electrode 40O and present widget 82M using visual configuration 132 as shown in FIG. 11.

Widget 82P. In FIG. 10, GUI 62 presents widget 82P using visual configuration 132. In response to medical professional 34 clicking on widget 82P, GUI 62 can select triplet of electrodes 40P, 40Q and 30R and present widget 82P using visual configuration 134 as shown in FIG. 11.

In a third embodiment, the example presented in FIG. 11 can immediately follow the example presented in FIG. 10. In this embodiment, GUI 62 can transition from the configuration presented in FIG. 10 to the configuration presented in FIG. 11 in response to medical professional 34 clicking on the following sequence of widgets 82:

Widget 82N. In FIG. 10, GUI 62 presents widgets 82N and 82O using visual configuration 134, indicating that triplets of electrodes 40N, 40O, 40P and 40O, 40P, 40Q are selected. In response to medical professional 34 clicking on widget 82N, GUI 62 can deselect electrodes 40P and 40Q (i.e., the GUI deselects electrode 40Q automatically) and present widgets 82N and 82O using visual configuration 132 as shown in FIG. 11.

Widget 82M. In FIG. 10, GUI 62 presents widget 82M using visual configuration 134. Upon processor 46 detecting medical professional 34 clicking on widget 82M, the processor can present widget 82M using visual configuration 132.

Widget 82P. In FIG. 10, GUI 62 presents widget 82P using visual configuration 132. In response to medical professional 34 clicking on widget 82P, GUI 62 can select electrode 40P and present widget 82P using visual configuration 134, as shown in FIG. 11.

As shown in FIG. 11, the electrode corresponding to icon 80O is not selected. Therefore, this example enables medical professional 34 to configure (i.e., via GUI 62) medical system 20 to perform IRE ablation with a gap (i.e., the area of tissue engaged by the electrode corresponding to icon 80O).

Figure 12:
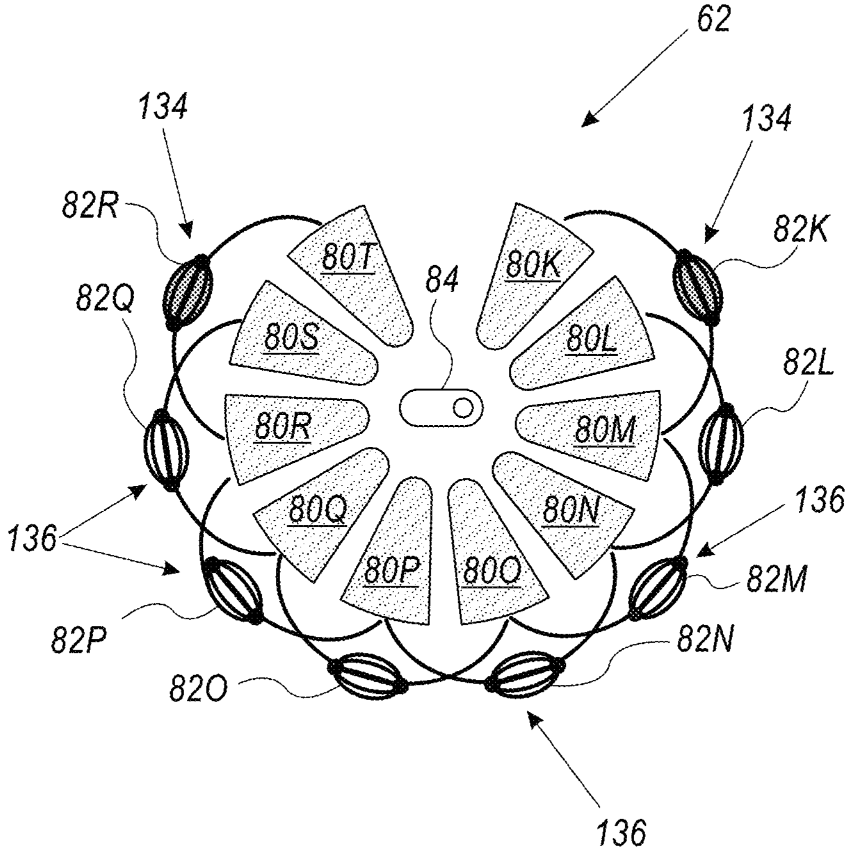

In the example presented in FIG. 12, in response to medical professional 34 clicking on widgets 82K-82R (i.e., all the triplet selection widgets in FIG. 12), processor 46 selects electrodes 40 corresponding to icons 80K-80T (i.e., all the icons in FIG. 12) for ablation. In this example, medical professional 34 clicks on all widgets 82K-82R (i.e., GUI 62 does not automatically "fill in" any of the widgets), and during the selection, GUI 62 prevents the medical professional from selecting any of the widgets that can result in uneven ablation by electrodes 40.

In the configuration shown in FIG. 12, GUI 62 presents widgets 82K and 82R using visual configuration 134, widgets 82L-82Q using visual configuration 136 and icons 80K-80T (i.e., all the icons in FIG. 12) with shading indicating that electrodes 40K-40T are selected for ablation. In an alternative embodiment, processor 46 can select electrodes 40 corresponding to icons 80K-80T in response to medical professional 34 "sliding" toggle widget from left to right, thereby selecting the electrodes corresponding to all the icons in FIG. 12.

Figure 13:
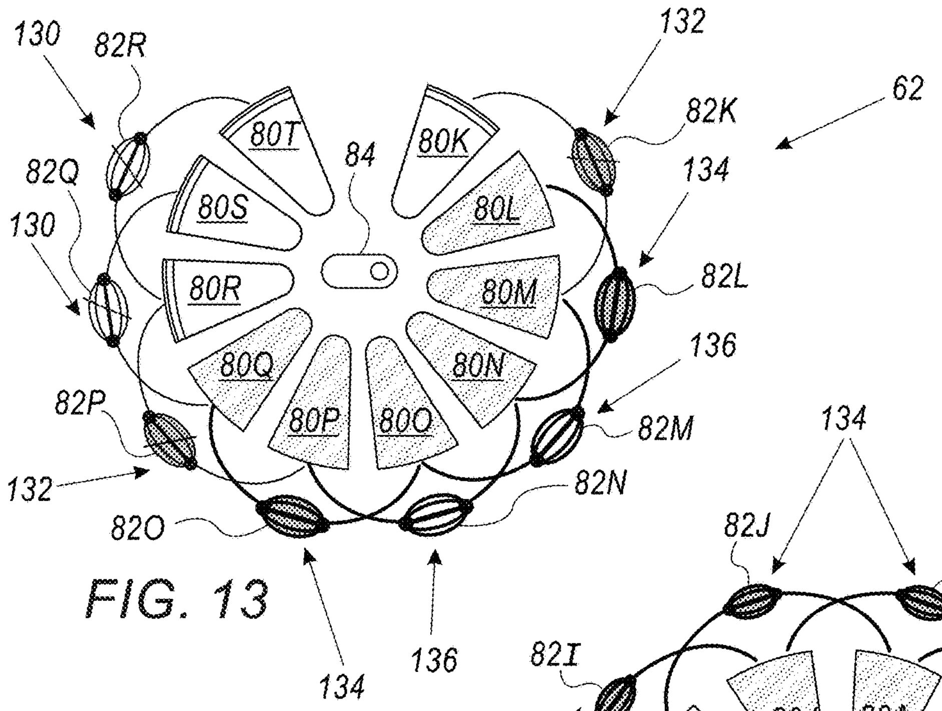

The example presented in FIG. 13 can immediately follow the example presented in FIG. 9. In this example, in response to medical professional 34 clicking on widgets 82L-82O, processor 46 selects electrodes 40 corresponding to icons 80L-80Q for ablation. In this example, GUI 62 presents widgets 82K and 82P using visual configuration 132, widgets 82L and 82O using visual configuration 134, widgets 82M and 82N using visual configuration 136, widgets 82Q and 82R using visual configuration 130, icons 80L-80Q with shading indicating that electrodes 40L-40Q are selected for ablation, and icons 80K and 80R-80T without shading. In this example, professional 34 clicks on all widgets 82L-82O (i.e., GUI 62 does not automatically "fill in" any of the widgets), and during the selection, GUI 62 prevents the medical professional from selecting any of the widgets that can result in uneven ablation by electrodes 40.

Figure 14:
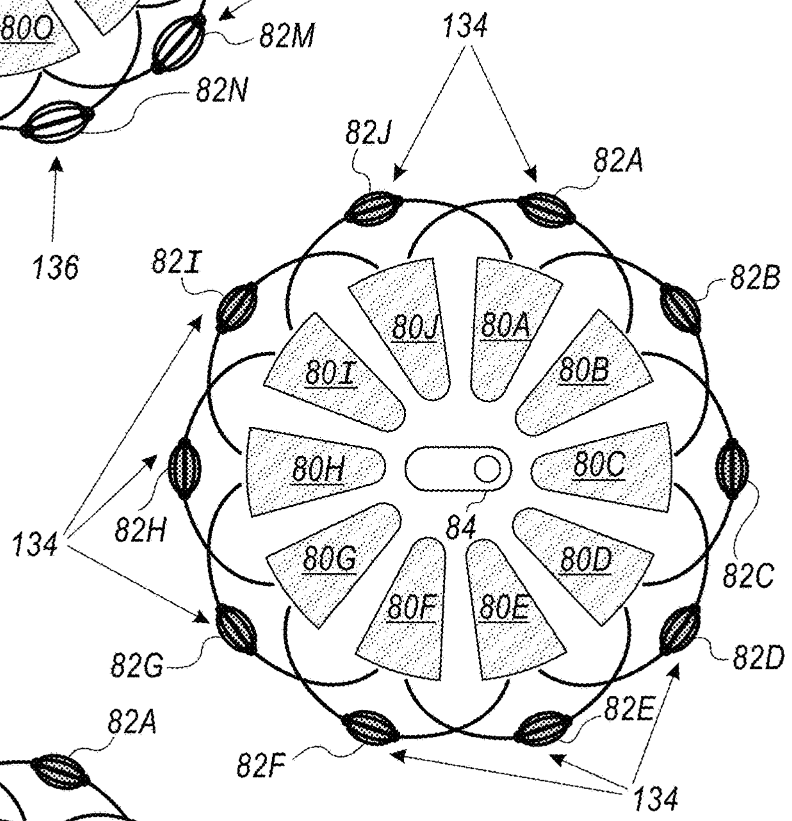

In the example presented in FIG. 14, in response to medical professional 34 clicking on widgets 82A-82J (i.e., all the triplet selection widgets in FIG. 14), processor 46 selects electrodes 40 corresponding to icons 80A-80J (i.e., all the icons in FIG. 14). In this example, GUI 62 presents widgets 82A-82J using visual configuration 134, and icons 80A-80J (i.e., all the icons in FIG. 14) with shading indicating that electrodes 40A-40J are selected for ablation. In an alternative embodiment, processor 46 can select electrodes 40 corresponding to icons 80K-80T in response to medical professional 34 "sliding" toggle widget 84 from left to right, thereby selecting the electrodes corresponding to all the icons in FIG. 14.

While both FIGS. 12 and 14 show the respective ablation selection statuses of all electrodes 40 as "selected", the toggle statuses of widgets 82 differ in the two figures. This is due to the different configurations of the electrode assemblies presented in those Figures. The electrode assembly presented in FIG. 12 corresponds to the lasso-shaped electrode assembly shown in FIG. 4 and the electrode assembly presented in FIG. 14 corresponds to the balloon-shaped electrode assembly shown in FIG. 2. In the balloon-shaped electrode assembly, a given widget 82 corresponding to a given group of the electrodes comprising electrodes 40A and 40J, none of the widgets for the lasso-shaped electrode assembly correspond to a group of the electrodes comprising electrodes 40K and 40T.

In some embodiments, medical professional 34 can select electrodes 40A-40J (i.e., to transition from the configuration of widgets 82 shown in FIG. 3 to the configuration shown in FIG. 14) by clicking at least four widgets 82. In one example, medical professional 34 can select electrodes 40A-40J by clicking one of the following sequence of widgets 82: 82A, 82B, 82C, 82D, 82E, 82F, 82G and 82H. Upon GUI 62 detecting this sequence, the GUI can automatically select widgets 80I and 80J in order to prevent a gap in ablation between electrodes 40I and 40J.

In another example, medical professional 34 can select electrodes 40A-40J by clicking on one of the following sequence of widgets 82:

82A, 82D, 82G and 82H. Upon detecting thus sequence, GUI 62 can then automatically "fill in" widgets 82B, 82C, 82E, 82F, 82I and 82J to select electrodes 40A-40J.

82A, 82D, 82G and 82I. Upon detecting thus sequence, GUI 62 can then automatically "fill in" widgets 82B, 82C, 82E, 82F, 82H and 82J to select electrodes 40A-40J.

82A, 82D, 82G and 82J. Upon detecting thus sequence, GUI 62 can then automatically "fill in" widgets 82B, 82C, 82E, 82F, 82H and 82I to select electrodes 40A-40J.

While the examples presented in both FIGS. 12 and 14 show GUI 62 selects all electrodes 40 in response to input received from medical professional 34, the respective visual configurations of the widgets are different in these two examples. In the example presented in FIG. 12, medical professional 34 must click on a given widget 82 to either select or deselect specific electrodes 40. For example, if electrodes 40K-40M are currently selected, GUI 62 will only enable medical professional 34 to click on widgets 82L (i.e., so as to select electrode 40N) and 82K (i.e., so as to deselect electrodes 40K-40M).

In the example presented in FIG. 14, electrodes 40A-40J were selected automatically by GUI 62. As described supra, medical professional 34 can select electrodes 40A-40J by either "sliding" toggle widget 84 from left to right, or by clicking on at least four widgets 82 as described in the examples hereinabove.

Figure 15:
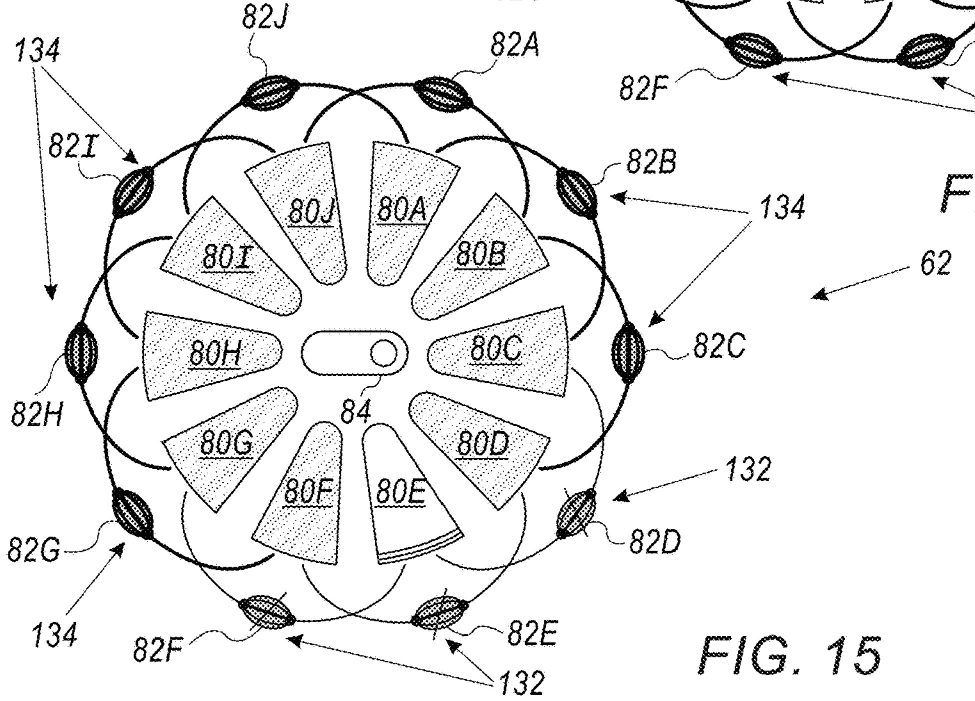

The example presented in FIG. 15 can immediately follow the example presented in FIG. 14. In this example, in response to medical professional 34 clicking on widget 82E, processor 46 can automatically "select" widgets 82D and 82F, thereby deselecting electrodes 40 corresponding to icon 80E).

In this example, electrodes 40D and 40F (i.e., respectively corresponding to icons 80D and 80F) are selected and electrode 40E (corresponding to icon 80E) is not selected, thereby creating a gap (i.e., for the ablation) in the region of tissue in contact with electrode 40E. As shown in FIG. 15, GUI 62 presents widgets 82A-82C and 82G-J using visual configuration 134, widgets 82D-F using visual configuration 132, icons 80A-80D and 80F-80J with shading (indicating that electrodes 40F-40J are selected for ablation) and icon 80E without shading.

Returning to the flow diagram, in a receive step 114, processor 46 receives an input indicating a selection of a given widget 82. In the configuration shown in FIG. 1, processor 46 can receive the input in response to medical professional 34 using input devices 66 or touchscreen 64 to click on the given widget. The given widget corresponds to a triplet of electrodes 40 that are in contact with a region of tissue in heart 26, and medical professional 34 can select the given widget in order to select or deselect the region of tissue (i.e., for IRE ablation).

In a first decision step 116, if the given widget can be selected (i.e., based on its toggle status), then in a third identification step 118, processor 46 identifies, in the triplet of electrodes 40 corresponding to the given widget, one or more of the electrodes, whose respective statuses need to be toggled (i.e., from selected to deselected or from deselected to selected) in response to the selection of the given widget. In embodiments described herein, a given widget can be selected if the given widget on display 64 comprises visual configuration 132 or 134.

In a toggle step 120, processor 46 toggles the ablation selection status (i.e., for ablation as described supra) of the identified one or more electrodes, and toggles, on display 64, a visual configuration of the corresponding one or more electrode icons 80 (e.g., from shaded to not shaded or from not shaded to shaded).

In a second decision step 122, if medical professional 34 has completed selection of electrodes 40, then in a delivery step 124, IRE ablation module 56 delivers IRE ablation energy to the selected electrodes. However, if the selection of electrodes 40 is not complete, then the method continues with step 106.

Returning to step 116, if the given widget cannot be selected, then the method continues with step 106. In embodiments described herein, a given widget cannot be selected if the given widget on display 64 comprises visual configuration 130 or 136.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
- grouping a set of electrodes disposed at a distal end of a medical probe and configured to contact tissue in a body cavity into a plurality of groups, each group comprising a plurality of adjacent electrodes;
- presenting, on a display, a set of selectable widgets having a one-to-one correspondence with the groups;
- receiving, by a processor, an input indicating selection of a given widget; and
- toggling, in response to the selection, an ablation selection status of one or more of the electrodes in the group corresponding to the given widget to selected or deselected based, at least in part, on a detection of an ablation selection status of one or more electrodes adjacent to, but not included in, the electrodes in the corresponding group, wherein the detected ablation selection status of the one or more adjacent electrodes determines which electrode or electrodes in the corresponding group are toggled.

2. The method according to claim 1, wherein one or more electrodes in the set of electrodes belongs to more than one of the plurality of groups.

3. The method according to claim 1, and further comprising identifying the ablation selection status for each of the electrodes in the set of electrodes, presenting, on the display, a set of icons having a one-to-one correspondence with each of the electrodes in the set of electrodes, wherein the presented icons comprise respective visual configurations of the ablation selection status of each of the electrodes in the set of electrodes.

4. The method according to claim 1, wherein the distal end is selected from a group consisting of a lasso, a basket, a balloon, and a deflectable element.

5. The method according to claim 1, and further comprising identifying a toggle status for each of the groups, wherein the toggle status for a given group indicates whether or not the ablation selection status of any of the electrodes in the given group can be toggled between a selectable and a non-selectable state, wherein the presented widgets comprise respective visual configurations of the toggle status of the widgets, and wherein receiving the toggle status of the given widget indicates that the ablation selection status of the electrodes in the corresponding group can be toggled.

6. The method according to claim 5, and further comprising presenting a toggle widget on the display, and wherein upon receiving an input selecting the toggle widget, setting the ablation selection status to the set of electrodes to the selectable state.

7. The method according to claim 5, and further comprising presenting a toggle widget on the display, and wherein upon receiving an input selecting the toggle widget, setting the ablation selection status to the set of electrodes to the non-selectable state.

8. The method according to claim 5, wherein the electrodes comprise ablation electrodes, and further comprising conveying ablation energy to the ablation electrodes having selectable states.

9. The method according to claim 8, wherein the ablation energy comprises irreversible electroporation.

10. The method according to claim 5, wherein selecting the given widget toggles the given widget between a widget selected state and a widget deselected state.

11. The method according to claim 10, wherein upon toggling the given widget from a widget deselected state to a widget selected state in response to the input and detecting that the ablation selection status of one or more electrodes adjacent to, but not included in, the electrodes in the group corresponding to the given widget are non-selected, setting the ablation selection status of the electrodes in the corresponding group to selected.

12. The method according to claim 10, wherein each of the groups comprise a pair of outer electrodes and one or more inner electrodes located between the pair of outer electrodes, and wherein upon toggling the given widget from a widget deselected state to a widget selected state in response to the input and detecting that the ablation selection status of one or more electrodes adjacent to, but not included in, the electrodes in the group corresponding to the given widget are selected, setting the ablation selection status of the one or more inner electrodes in the corresponding group to selected.

13. The method according to claim 10, wherein each of the groups comprise a pair of outer electrodes and one or more inner electrodes located between the pair of outer electrodes, and wherein upon toggling the given widget from a widget deselected state to a widget selected state in response to the input, detecting that the ablation selection status of a first given electrode adjacent to a first outer electrode, but not included in the electrodes in the group corresponding to the selected widget is selected, and detecting that the ablation selection status of a second given electrode adjacent to a second outer electrode, but not included in the electrodes in the corresponding group is non-selected, setting the ablation selection status of the first outer electrode adjacent to the first given electrode to selected.

14. The method according to claim 10, wherein upon toggling the given widget from a widget selected state to a widget deselected state in response to the input and detecting that the ablation selection status of one or more electrodes adjacent to, but not included in, the electrodes in the group corresponding to the given widget are non-selected, setting the ablation selection status of the electrodes in the corresponding group to deselected.

15. The method according to claim 10, wherein each of the groups comprise a pair of outer electrodes and one or more inner electrodes located between the pair of outer electrodes, and wherein upon toggling the given widget from a widget selected state to a widget deselected state in response to the input and detecting that the ablation selection status of one or more electrodes adjacent to, but not included in, the electrodes in the group corresponding to the given widget are selected, setting the ablation selection status of the one or more inner electrodes in the corresponding group to deselected.

16. The method according to claim 10, wherein each of the groups comprise a pair of outer electrodes and one or more inner electrodes located between the pair of outer electrodes, and wherein upon toggling the given widget from a widget selected state to a widget deselected state in response to the input, detecting that the ablation selection status of a first given electrode adjacent to a first outer electrode, but not included in the electrodes in the group corresponding to the selected widget is selected, and detecting that the ablation selection status a second given electrode adjacent to a second outer electrode, but not included in the electrodes in the corresponding group is non-selected, setting the ablation selection status of the first outer electrode adjacent to the first given electrode to deselected.

17. An apparatus, comprising:

an invasive medical probe configured to be inserted into a body cavity and comprising a set of electrodes disposed at a distal end of the probe and configured to contact tissue in the body cavity;

a display; and a processor configured:

to group the set of electrodes into a plurality of groups of adjacent electrodes, to present, on the display, a set of selectable widgets having a one-to-one correspondence with the groups, to receive an input indicating selection of a given widget, and to toggle, in response to the selection, an ablation selection status of one or more of the electrodes in the group corresponding to the given widget to selected or deselected based, at least in part, on a detection of an ablation selection status of one or more electrodes adjacent to, but not included in, the electrodes in the corresponding group, wherein the detected ablation selection status of the one or more adjacent electrodes determines which electrode or electrodes in the corresponding group are toggled.

18. A computer software product, operated in conjunction with a medical probe configured to be inserted into a body cavity and comprising a set of electrodes disposed at a distal end of the probe and configured to contact tissue in the body cavity, the product comprising a non-transitory computer-readable medium, in which program instructions are stored, which instructions, when read by a computer, cause the computer:

to group the set of electrodes into a plurality of groups of adjacent electrodes;

to present, on a display, a set of selectable widgets having a one-to-one correspondence with the groups;

to receive an input indicating selection of a given widget; and to toggle, in response to the selection, an ablation selection status of one or more of the electrodes in the group corresponding to the given widget to selected or deselected based, at least in part, on a detection of an ablation selection status of one or more electrodes adjacent to, but not included in, the electrodes in the corresponding group, wherein the detected ablation selection status of the one or more adjacent electrodes determines which electrode or electrodes in the corresponding group are toggled.

* * * * *